US005780030A

United States Patent [19]

Simon et al.

[11] Patent Number: 5,780,030
[45] Date of Patent: *Jul. 14, 1998

[54] PASSIVE VACCINE AGAINST LYME DISEASE

[75] Inventors: Markus M. Simon; Ulrich E. Schaible; Klaus Eichmann, all of Freiburg; Michael Kramer; Wallich Reinhard, both of Heidelberg, all of Germany

[73] Assignees: Max-Planck-Gesellschaft zur Forderung der Wissenschaften e.V., Gottingen; Deutsches Krebsforschun Zentrum Stiftung des Offentlichen Rechts, Heidelberg, both of Germany

[ * ] Notice: The term of this patent shall not extend beyond the expiration date of Pat. No. 5,178,859.

[21] Appl. No.: 406,623

[22] Filed: Mar. 20, 1995

Related U.S. Application Data

[62] Division of Ser. No. 68,063, May 27, 1993, Pat. No. 5,434,077, which is a division of Ser. No. 937,054, Aug. 26, 1992, abandoned, which is a division of Ser. No. 585,310, Sep. 19, 1990, Pat. No. 5,178,859.

[30] Foreign Application Priority Data

Sep. 19, 1989 [DE] Germany ..................... 39 31 236.4
May 17, 1990 [DE] Germany ..................... 40 15 911.6

[51] Int. Cl.$^6$ .................... A61K 39/395; C07K 15/28
[52] U.S. Cl. .................... 424/150.1; 424/234.1; 435/70.21; 435/172.2; 435/340; 530/388.4; 530/389.5
[58] Field of Search ................ 427/139.1, 147.1, 427/159.1, 150.1, 234.1, 164.1; 435/69.1, 70.21, 172.2, 172.3, 240.3, 340; 530/387.9, 388.4, 389.5

[56] References Cited

U.S. PATENT DOCUMENTS 5,034,515  7/1991  Proctor ..................... 536/1.1
5,523,089  6/1996  Bergstrom et al. ............ 424/262.1

FOREIGN PATENT DOCUMENTS 0252641  of 0000  European Pat. Off. .
0492964  of 0000  European Pat. Off. .
WO9004411 of 0000  WIPO .
WO9109870 of 0000  WIPO .
WO9200055 of 0000  WIPO .
WO9307897 of 0000  WIPO .
WO9308299 of 0000  WIPO .

OTHER PUBLICATIONS

Schaible et al., Monoclonal antibodies specific for the outer surface protein A (OspA) of *Borrelia burgdorferi* prevent *Lyme borreliosis* in severe combined immunodeficiency (Scid mice), Proc. Natl. Acad. Sci. 82: 3768–3772 (May 1990).

Schaible et al., "The severe combined immunodeficiency (Scid) mouse." J. Exp. Med. 170: 1427–1432 (Oct. 1989).

Wallach et al., Evaluation of genetic divergence among *Borrelia Burgdorferi* isolates by use of OSPA, fla, MSP60, and MSP70 gene products. Infection and Immunity. 4856–4866 (Nov. 1992).

Benach et al., "Biological activity of *Borrelia burgdorferi* antigens." Ann. N.Y. Acad. Sci. 539: 115–125 (1988).

Craft et al., "Antigens of *Borrelia burgdorferi* recognized during Lyme disease." J. Clin. Immunol. 934–939 (Oct. 1986).

Alan C. Steere. "Lyme Disease." The New England Journal of Medicine. 586–595 (Aug. 31, 1986).

Simon et al., "A mouse model for *Borrelia burgdorferi* infection: –approach to a vaccine against Lyme disease", Immunology Today, vol. 12, No. 1, p. 11 (1991).

Schaible et al., "Monoclonal antibodies specific for the outer–surface protein A (OspA) of *Borrelia burgdorferi* prevent *Lyme borreliosis* in severe combined immunodeficiency (scid) mice", Proc. Natl. Acad. Sci. USA, vol. 87, pp. 3768–3772, May 1990.

Fikrig et al., "Protection of Mice Against the Lyme Disease Agent–by Immunizing with Recombinant OspA", Science, p. 553, Oct. 1990.

Bergstrom et al., "Molecular Analysis of linear plasmid–encoded–major surface proteins. OspA and OspB, of the Lyme Disease spirochaete *Borrelia burgdorferi*", Molecular Microbiology, vol. 3, No. 4, pp. 479–486 (1989).

Lane et al., "Antigenic Characteristics of *Borrelia burgdorferi*–isolated from Ixodid Ticks in California". J. Clinical Microbiology, pp. 2344–2349, Oct. 1989.

Wallich et al., "Cloning and sequencing of the gene encoding–the outer surface protein A (OspA) of a European *Borrelia burgdorferi* isolate", Nucleic Acids Research, Nov. 1989.

Schaible et al., "Demonstration of Antigen–Specific T Cells and–Histophatological Alterations in Mice Experimentally Inoculated with *Borrelia burgdorferi*", pp. 41–47, Jan. 1989.

Johnson et al., "Experimental Infection of the Hamster with–*Borrelia burgdorferi*". Annals of the New York Academy of Sciences, p. 258 (1987).

Howe et al., "Organization of Genes Encoding Two Outer Membrane–Proteins in the Lyme Disease Agent *Borrelia burgdorferi* within a Single Transcription Unit". Infection and Immunity, p. 207, Oct. 1986.

Howe et al., "A Single Recombinant Plasmid Expressing Two Major–Outer Surface Proteins of the Lyme Disease Spirochete". Science, vol. 227 p. 645, Feb. 1985.

(List continued on next page.)

Primary Examiner—Lila Feisee
Assistant Examiner—Julie E. Reeves
Attorney, Agent, or Firm—Felfe & Lynch

[57] ABSTRACT

The present invention provides a vaccine against Lyme disease, wherein it contains one or more monoclonal antibodies which are specific for the 31 kD antigen (OspA) or the 34 kD antigen (OspB) of *Borrelia burgdorferi*. The present invention also provides a process for obtaining this vaccine, as well as new monoclonal anti-bodies and antigens.

6 Claims, 2 Drawing Sheets

OTHER PUBLICATIONS

Barbour et al., "Heterogeneity of Major Proteins in Lyme Disease–*Borrelia burgdorferi* A Molecular Analysis of North American and European Isolates", *J. Infectious Diseases*, vol. 152, No. 3, p. 478, Sep. 1985.

Seaver 1994 Geretic Engineering, vol. 14(14): 10 and 21.

Dorlands Pocket Medical Dictionary 22nd Ed. 1977 p. 696.

Howe et al 1986 Infection & Immunity vol. 54 (1): 207–212.

Wilske et al 1988 Annals NY Acad Sci vol. 539: 126–143.

FIG. 1

```
atgaaaaaatatttattgggaataggtctaatattagccttaatagcatgtaagcaaaat
 M  K  K  Y  L  L  G  I  G  L  I  L  A  L  I  A  C  K  Q  N gttagcagccttgacgagaaaaacagcgtttcagtagatttgcctggtgaaatgaacgtt
 V  S  S  L  D  E  K  N  S  V  S  V  D  L  P  G  E  M  N  V cttgtaagcaaagaaaaaacaaagacggcaagtacgatctaattgcaacagtagacaag
 L  V  S  K  E  K  N  K  D  G  K  Y  D  L  I  A  T  V  D  K cttgagcttaaaggaacttctgataaaaacaatggatctggagtacttgaaggcgtaaaa
 L  E  L  K  G  T  S  D  K  N  N  G  S  G  V  L  E  G  V  K gctgacaaaagtaaagtaaaattaacaatttctgacgatctaggtcaaaccacacttgaa
 A  D  K  S  K  V  K  L  T  I  S  D  D  L  G  Q  T  T  L  E gttttcaaagaagatggcaaaacactagtatcaaaaaagtaacttccaaagacaagtta
 V  F  K  E  D  G  K  T  L  V  S  K  K  V  T  S  K  D  K  S tcaacagaagaaaaattcaatgaaaaaggtgaagtatctgaaaaaataataacaagagca
 S  T  E  E  K  F  N  E  K  G  E  V  S  E  K  I  I  T  R  A gacggaaccagacttgaatacacagaaattaaaagcgatggatctggaaaagctaaagag
 D  G  T  R  L  E  Y  T  E  I  K  S  D  G  S  G  K  A  K  E gttttaaaaagctatgttcttgaaggaactttaactgctgaaaaaacaacattggtggtt
 V  L  K  S  Y  V  L  E  G  T  L  T  A  E  K  T  T  L  V  V aaagaaggaactgttactttaagcaaaaatatttcaaaatctggggaagtttcagttgaa
 K  E  G  T  V  T  L  S  K  N  I  S  K  S  G  E  V  S  V  E cttaatgacactgacagtagtgctgctactaaaaaaactgcagcttggaattcaggcact
 L  N  D  T  D  S  S  A  A  T  K  K  T  A  A  W  N  S  G  T tcaactttaacaattactgtaaacagtaaaaaaactaaagaccttgtgtttacaaaagaa
 S  T  L  T  I  T  V  N  S  K  K  T  K  D  L  V  F  T  K  E aacacaattacagtacaacaatacgactcaaatggcaccaaattagaggggtcagcagtt
 N  T  I  T  V  Q  Q  Y  D  S  N  G  T  K  L  E  G  S  A  V gaaattacaaaacttgatgaaattaaaaacgctttaaaataa
 E  I  T  K  L  D  E  I  K  N  A  L  K  *
```

PASSIVE VACCINE AGAINST LYME DISEASE

This application is a Divisional of Ser. No. 08/068,063 filed May 27, 1993, now U.S. Pat. No. 5,434,077, which in turn is a Divisional of Ser. No. 07/937,054 filed Aug. 26, 1992, now abandoned which in turn is a Divisional of Ser. No. 07/585,310, filed 9/19/90, now U.S. Pat. No. 5,178,859.

The present invention is concerned with a vaccine against Lyme disease, with a process for obtaining said vaccine, with new monoclonal antibodies, with new antigens and with new recombinant DNA's and vectors.

Lyme borreliosis is the most common infectious disease transmitted by ticks in the temperate regions. It is caused by the spirochete *Borrelis burgdorferi* which is transmitted to humans in particular by ticks of the genus Ixodes. The disease is a chronic, progressive infection which attacks many organs, such as the skin, the central and peripheral nervous system, the heart, the liver, the kidneys and musculoskeletal system. Since a reliable treatment of this disease by therapy with antibiotics is difficult, at the moment great efforts are being made to investigate the pathogen itself and the immune response of the host to infection with *Borrelia burgdorferi*. In the case of persons afflicted by lyme disease, there is admittedly ascertained a high titre of antibodies against *Borrelia burgdorferi* which, however, do not provide any protection against the infection. It is assumed that the pathogen passes over very quickly from the blood circulation into the tissues and can there no longer be directly reached by the immune system. This would mean that a protection by antibodies is only possible immediately after commencement of the infection, i.e. as long as the pathogen is still present in the blood circulation.

The fact that a natural infection with *Borrelia burgdorferi* has been found in various kinds of animals has led to attempts to establish laboratory models for Lyme disease. This also took place with limited success. Thus, in the case of experiments which had the object of inducing in mice a specific immune response for *Borrelia burgdorferi*, it was found that the infection of inbred mouse strains with a prolonged cultured isolate of *Borrelia burgdorferi* led to moderate but significant pathomorphological changes in various organs, such as the brain, the heart, the lungs and the kidneys, which were comparable to those which are to be observed in patients with Lyme disease (see Schaible et al., Infect. Immun., 1, 41/1988). The development of a serious aspect of the disease in animals was presumably prevented either by the immune defense of the host and/or by the reduced virulence of spirochetes cultured in vitro for a comparatively long period of time (see Johnson et al., J. clin licrobiol.20, 747/1984; Schwan et al., Infect . and Immun., 56, 1837/1988).

It is an object of the present invention to provide an effective vaccine against Lyme disease. However, for this purpose, it is first necessary to develop an appropriate animal laboratory model. It is now suggested that a mouse strain without functionable T- and B-cells, the so-called scid mouse (see Bosma et al., Nature, 10, 52/1983) can serve as experimental animal since scid mice, in the case of infection with a pathogenic *Borrelia burgdorferi* isolate, develop & multi-systemic disease, namely, mainly polyarthritis and carditis. By means of this animal model,it is possible for the first time to test the action of vaccines against Lyme disease.

One subject of the present invention is a passive vaccine against Lyme disease which contains one or more specific monoclonal antibodies for the 31 kD antigen (OspA) and/or the 34 kD antigen (OspB) of *Borrelia burgdorferi* and especially OspA and/or OspB of *Borrelia burgdorferi* of the strain B31 (ATCC 35210) and/or ZS7 (DS p 5527). A vaccine is preferred which contains one of the antibodies of the class IgG according to the present invention and especially preferably of the subclass IgG2b or IgG1. Surprisingly, in contradistinction to the administration of another antibody, for example against the 41 kD surface antigen of *Borrelia burgdorferi* (flagellin), the administration of the antibody according to the present invention has the result,in the case of immune-deficient experimental animals and preferably of scid mice which have been infected with viable pathogenic *Borrelia burgdorferi* and preferably with *Borrelia burgdorferi* ZS7, that the development of arthritis, carditis and hepatitis is completely or at least substantially prevented.

The vaccine according to the present invention with the antibody as active material can possibly also contain conventional carrier, filling and adjuvant materials.

Furthermore, the present invention provides a process for obtaining a passive vaccine against Lyme disease from lymphocytes or spleen cells of an experimental animal, preferably of a mouse, which has been immunised with *Borrelia burgdorferi* organisms or.parts thereof, preferably with complete *Borrelia burgdorferi* B31 and/or ZS7 organisms, in which, from the lymphocytes or spleen cells of the immunised animals, there is obtained, by cell fusion, a hybridoms which produces a monoclonal antibody according to the present invention.

Thus, a subject of the present invention is also a hybridoma cell line (ECACC 89091302) which produces an antibody LA-2 against OspA (IgG2b) according to the present invention. Furthermore, the subject of the present invention is also the hybridoma cell line ECACC 90050406 producing the antibody LA—26.1 against OspA (IgG1), as well as the hybridoma cell lines ECACC 90050405 and ECACC 90050407 producing antibodies LA—25.1 and LA-27.1, respectively,against OspB (IgG2b and IgG1, respectively).

Furthermore, the present invention provides the pathogenic *Borrelia burgdorferi* strain ZS7 (DSM 5527).

In addition, the subject of the present invention is an antigen which immune-reacts with a monoclonal antibody according to the present invention. By this is to be understood an antigen which contains the whole amino acid sequence of OspA or OspB or also only an immunogenically-acting part sequence (immunogenic epitope) of OspA or OspB, respectively. Potentially immunogenic epitopes of these proteins can be determined without difficulty by a structural analysis of the OspA protein, for example a Chou-Fasm analysis, and then tested experimentally for their effectiveness.

Yet another subject of the present invention is also, in particular,. a recombinant antigen which immune-reacts with the antibody according to the present invention in which the DNA sequence coding for the antigen is present on a recombinant vector, preferably a prosaryotic vector, which is suitable for the protein expression.

In particular, a subject of the present invention is an antigen from *Borrelia burgdorferi* ZS7 which specifically immune-reacts with the antibody according to the present invention and which contains the amino acid sequence shown in FIG. 1 of the accompanying drawings or an immunogenic epitope of this sequence. Consequently, the present invention also concerns a recombinant DNA which contains (1) the sequence shown in FIG. 1, (2) a nucleic acid sequence corresponding to it in the scope of the degeneration of the genetic code or (3) one hybridising under stringent conditions with a sequence from (1) and/or (2), which sequence codes for the 31 kD antigen of *Borrelia burgdorferi* strain ZS7 or an immunogenic epitope thereof. The term stringent hybridising conditions is thereby to be understood as in Maniatis et al., Molecular Cloning, A Laboratory manual (1982), Cold Spring Harbor Laboratory, New York.

Especially preferred is an antigen according to the present invention which is a recombinant non-fusion protein or β-galactosidase fusion protein.

Furthermore, the present invention is concerned with a recombinant vector which contains one or more copies of a recombinant DNA according to the present inventions The vector according to the present invention can be a prokaryotic and/or eukaryotic vector.but is preferably a prokaryotic vector. The recombinant vector can be present extrachromosomally in the host cell (for example plasmid) or it can also be integrated in the genome of the host cell (for example bacteriophage lambda). The vector according to the present invention is preferably a plasmid, the recombinant vector pZS-7/31-2 (DSM 5528) being especially preferred.

The present invention also provides a process for obtaining antigens according to the present invention by investigation of a *Borrelia burgdorferi* gene bank with one or more antibodies according to the present invention in which the clones are isolated which show a positive immune reaction with the antibodies used.

Since the antigen according to the present invention itself also can be used for active immunisation, i.e. for the induction of antibody formation in the organism, the present invention also provides an active vaccine against Lyme disease which, as active material, contains an antigen according to the present invention, optionally together with conventional carrier, filling and adjuvant materials. A preferred embodiment is when the antigen according to the present invention is obtained gene-technologically.

Indeed, it could be shown that the administration of native or recombinant OspA to normal mice induces the formation of protective antibodies which, after passive transfer into scid mice, protect these against Lyme borreliosis. In particular, it is found that recombinant OspA induces a protective immune response comparable with native OspA and, therefore, represents a highly promising candidate for a vaccine against Lyme borreliosis in humans.

The present invention also provides a process for obtaining a passive vaccine against Lyme disease in which experimental animals, preferably mice, are immunised with an antigen according to the present invention and protective, polyclonal or monoclonal antibodies are obtained in the usual way from the immunised experimental animals.

Finally, the present invention also provides a process for the isolation and reculturing of pathogenic *Borrelia burgdorferi* organisms, wherein, from immune-deficient experimental animals, preferably mice, which have previously been infected with the pathogen, there is obtained the pathogen, whereby the pathogeneity of the pathogen is retained. Especially preferred is a process in which pathogenic *Borrelia burgdorferi* strain ZS7 (DST 5527) organisms are obtained from the blood and/or joints of infected scid mice.

The following examples are given for the purpose of illustrating the present, reference being made to the accompanying drawings.

BRIEF DESCRIPTION OF THE DRAWINGS

FIG. 1 shows the DNA and amino acid sequence of the 31 kD antigen (OspA) from *Borrelia burgdorferi* strain ZS7 and FIG. 2 shows the immunological characterisation of the recombinant protein rZS7/31-2.

Figure 2:
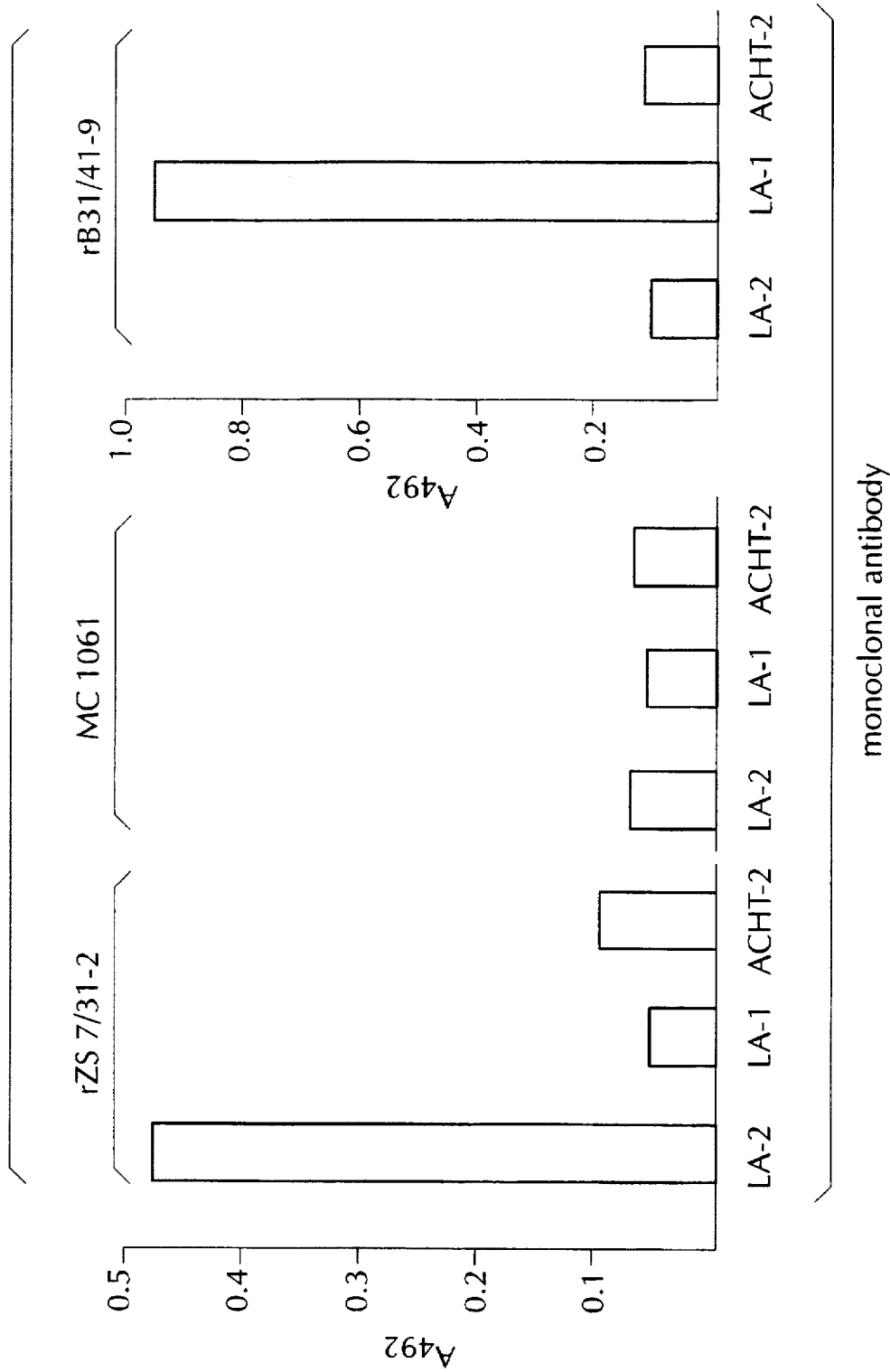

EXAMPLE 1.

Induction of arthritis, carditis and hepatitis in scid mice by infection with *Borrelia burgdorferi* strain ZS7 Treatment of the mice with *Borrelia burgdorferi*.

Adult mice of the strains C.B-17 scid (homozygous for the scid mutation) and C.B-17 were injected subcutaneously into the root of the tail with $1 \times 10^5$, $5 \times 10^5$, $1 \times 10^6$ or $1 \times 10^8$ viable or killed (ultra-violet irradiation) *Borrelia burgdorferi* organisms.

Isolation of *Borrelia burgdorferi* from ticks and mice.

The investigations were carried out with the *Borrelia burgdorferi* strain B31 (ATCC 35210), already cultured for a long time, and the fresh isolate *Borrelia burgdorferi* strain ZS7 (DSM5527) which had been isolated from a female Ixodes rizinus tick. All *Borrelis burgdorferi* strains were cultured in modified Kelly' medium (see Barbour et al., Switzerland Curr. Microbiol., 8, 123/1983). *Borrelia burgdorferi* organisms which had been obtained from the midgut of ticks sterilised with ethanol or from the blood of infected mice were initially cultured in Kelly's medium with the addition of 8 μg./ml. of kanamycin and 230 μg./ml. fluorouracil (see Johnson et al., J. Clin. Microbiol., 1., 81/1984). Serological tests.

The detection of *Borrelia burgdorferi*-specific antibodies was carried out in a conventional ELISA process (see Justus et al., Wehrmed. Mschr., 32, 263/1988). The standard curve for the content of immuno globulin (Ig) was obtained by coating a dish with anti-mouse Ig (1:500 dilution of the serum solution of Paesel, Frankfurt, Federal Republic of Germany) and titration of the total mouse IgG or IgM content (Calbiochem, La Jolla, U.S.A.). Total serum IgM and IgG were measured in a similar manner. The concentration of *Borrelia burgdorferi*-specific IgM or IgG antibodies is given in μg. Ig/ml. of serum.

Immunofluorescence and Giemsa staining.

50 1μl. of blood were pipetted into a haemocrit testtube (Becton and Dickinson, Heidelberg, Federal Republic of Germany) and centrifuged 5000 g in a haemocrit centrifuge (ECCO, Federal Republic of Germany). The test tubes were cut up on the interphase between serum and erythrocytes and 5 μl. of the serum were applied to microscope slides (Superior , Bad Mergentheim, Federal Republic of Germany). The microscope slides loaded with the serum samples were dried in the air and fixed in 100% ethanol for 1 minute at −20 C. After incubation for 1 hour with rabbit anti-*Borrelia burgdorferi* hyperimmune serum (1:100 dilution) at ambient temperature, with microscope slides were washed five times in PBS and then stained for 1 hour with FITC-conjugated goat anti-rabbit antiserum (1:20 dilution, Jackson Lab., West Grove, U.S.A.). The microscope slides were washed and embedded in Kaiser's glycerol gelatine (Merck, Darmstadt, Federal Republic of Germany) and immediately investigated by fluorescence microscopy. Untreated blood droplets were dried in the air, fixed in methanol, stained with Giemsa's stain (0.1%, Merck, Darmstadt, Federal Republic of German y), decolorised in PBS and embedded in Entellan (Merck, Darmstadt, Federal Republic of Germany).

Histological Preparations and Staining Processes,

Various internal organs (brain, heart, lungs, liver, kidneys, spleen and joints) were removed from mice previously infected with *Borrelia burgdorferi* at different times after the infection and stored either in liquid nitrogen for the preparation of frozen sections or in 5% formaldehyde (in PBS) for embedding in paraffin or methacrylate. Sections of 4 to 7 µm. thickness were prepared, stained with haemotoxylineosin and embedded in Entellan (Merck, Darmstadt, Federal Republic of Germany). The immunohistology was carried out with the use of streptavidin-biotin-peroxidase system (see Kramer et al., Eur. J. Immunol., 19, 151/1989).

Table 1 shows that *Borrelia burgdorferi* organisms of the isolates ZS7 and B31 were detected during the whole of the experimental period in the blood of scid mice which had previously been inoculated with viable organisms. However, only spirochetes of strain ZS7 but not of strain B31 could be recultured in vitro. In the case of comparison of the rec ultured organisms with the primary *Borrelia burgdorferi* ZS7 isolate, no changes in the protein content or in the plasmid profile could be ascertained. No or only extremely small titres of irrelevant antibodies were detected in scid mice infected with *Borrelia burgdorferi* during the entire period of observation. No IgM or IgG antibodies specific for 20 days after infection with *Borrelia burgdorferi*, scid mice showed the first clinical symptoms of arthritis (reddening and swelling of both tibiotarsal joints), which increased in the course of time. On the other hand, no symptoms of arthritis were found in scid mice which had been infected either with ultra-violet irradiated *Borrelia burgdorferi* organisms (ZS7) or with viable *Borrelia burgdorferi* organisms (B31) in C.B-17 control mice which had been infected with viable *Borrelia burgdorferi* ZS7 organisms.

Arthritic joint chances were also detected histopathologically in scid mice which had been infected with viable *Borrelia burgdoriferi* organisms (ZS7) (see. Table 1). Severe joint damages were ascertained, characterised by the presence of hyperplastically inflamed synovial lirin g cells, combined with erosion and destruction of cartilaginous tissue and/or bone. Furthermore, there was ascertained pan-carditis with infiltration of mono-nuclear cells in the endocardium, niyocardium and peri-cardium. There was also ascertained a progressive inflammation of the liver in which there was observed an infiltration of mononuclear cells, which was limited to the portal artery region and the central veins, granulomatous reactions and, finally, the appearance of liver fibrosis . In addition, smaller damage in the kidneys, the lungs, the brain and the striated musculature were ascertained.

TABLE 1

Infection of C.B-17 scid mice and C.B-17 control mice with *Borrelia burgdorferi*; reisolation of Spirochaetes from the tissue; antibody titre and formation of arthritis

| mouse strain | *B. burgdorferi* strain | number in infection | days after infection | *B. burgdorferi* detection in the blood+ | isolation | arthritis clinical | histo-pathological | antibody (µg/ml)°° total Ig µ | total Ig γ | specific Ig µ | specific Ig γ |
|---|---|---|---|---|---|---|---|---|---|---|---|
| C.B-17 | ZS7 | 5 × 10⁵ | 7 | + | − | − | − | − | 20 | − | − |
|  |  |  | 36 | + | +B | + | + | − | 21 | − | − |
|  |  |  | 49 | + | +B | + | + | − | 26 | − | − |
|  |  |  | 59 | + | +B | + | + | − | 396 | − | − |
|  | ZS7 | 1 × 10⁶ | 7 | + | − | + | + | − | 108 | − | − |
|  |  |  | 23 | + | +B | + | + | − | 54 | − | − |
|  | ZS7 | 1 × 10⁸ | 22 | + | − | + | + | − | 41 | − | − |
|  |  |  | 29 | + | +J | + | + | − | − | − | − |
|  |  |  | 87 | + | +B/J | + | + | − | − | − | − |
|  | ZS7 | 1 × 10⁵ | − | nd | nd | + | nd | nd | nd | nd | nd |
|  |  | 1 × 10⁶ | − | nd | nd | + | nd | nd | nd | nd | nd |
|  |  | 1 × 10⁸ | 16 | + | + | + | + | − | − | − | − |
|  | ZS7uv₄ | 1 × 10⁸ | 16 | − | − | − | − | − | − | − | − |
|  | B31 | 1 × 10⁸ | 22 | + | − | − | − | 26 | 37 | − | − |
|  |  |  | 29 | + | − | − | − | − | − | − | − |
|  | − |  | 22 | − | − | − | − | − | 47 | − | − |
|  | − |  | 29 | − | − | − | − | 54 | 364 | − | − |
| C.B-17 | ZS7 | 1 × 10⁸ | 16 | − | − | − | − | 2.515 | 5.963 | 438 | 56 |
| (n = 7) |  |  | 24 | − | − | − | − | 2.145 | 6.374 | 506 | 94 |
|  | − | − | − | − | − | − | − | 304 | 3.804 | − | − |
|  | − | − | − | − | − | − | − | 216 | 1.952 | − | − |

+ = by Giemsa staining or immunofluorescence
+ = isolation from blood (B), joint (J)
o+ = reddening and swelling of the tibiotarsal joint
oo− = <7.5 µg/ml. serum

*Borrelia burgdorferi* could be found in these animals (see Table 1). On the other hand, all C.B-17 control mice, which had been infected with *Borrelia burgdorferi*, expressed large amounts of total Ig and increased titres of IgM and IgG antibodies specific for *Borrelia burgdorferi*. Between 7 and

EXAMPLE 2.

Action of a monoclonal antibody specific for the *Borrelia burgdorferi* 31 kD antigen on the course of lyme borreliosis in scid mice. Preparation of the monoclonal antibody.

In the case of immunisation of a mouse which has an intact immune system with Borrelia burgdorferi organisms, polyclonal antibodies are expressed which are specific for Borrelia burgdorferi (see Table 1).

Ten week old female mice of the inbred strain BALB/c were immunised with Borrelia organism (Borrelia burgdorferi, strain B31; ATCC 35210) homogenised by sonication.

Immunisation protocol:
- day 0: 200 µg. Borrelia antigen in complete Freund's adjuvant subcutaneously
- day 21, 35, 49, 63: challenge with 100 µg. Borrelia antigen in phosphate-buffered saline (PBS) intraperitoneally
- day 66: removal of the spleen and preparation of a suspension of individual cells The immune spleen cells were fusioned with the Ag8-PAI myeloms cell line by standard methods with the use of polyethylene glycol (see J. H. Peters, H. Baumgarten, M. Schulze, "Monoklonale Antikörper", pub. Springer Verlag, Heidelberg).

The fusion products were seeded out into 96 well tissue culture plates. A pter 8 days, the cell culture supernatants were investigated for the presence of Borrelia burgdorferi-specific monoclonal antibodies with the help of a solid-phase ELISA (see J. H. Peters et al., loc. cit.).

The hybridoma cells from antibody-producing cultures were cloned according to the marginal dilution method. The culture supernatants of individual clones were subsequently again characterised in the solid-phase ELISA, as well as by Western blot analysis and by immunofluorescence investigations. The monoclonal antibody LA-2 of the subclass IgG2b is produced by a monoclonal hybridome line and secreted and reacts in the Western blot with the 31 kDa structure (OspA) of all investigated Borrelia burgdorferi strains (inter alia the isolates ZS7 and B31) in the case of contact with Borrelia burgdorferi proteins separated electrophoretically via an SDS gel and transferred by means of Western blot to a membrane. The monoclonal antibodies LA-26.1 (anti-OspA IgG1), LA 25.1 (anti-OspB (34 kDa antigen); IgG2b) and LA 27.1 (anti-OspB (34 kDa antigen) IgG1) were prepared and characterised in an analogous manner.

Infection of Mice with Borrelia burgdorferi ZS7.

C.B-17 scid mice were infected subcutaneously in the root of the tail with 1×10$^8$ viable Borrelia burgdorferi organisms (ZS7).

Treatment of the Mice with Antisera.

The infected scid mice were treated twice a week with various antisera. One group was treated with NMS (normal mouse serum), the second group with IMS (immune mouse serum) and the third group with the monoclonal antibody LA-2 (against the 31 kD antigen of Borrelis bergdorferi). The dosage of the administered antisera was 100 µl. or 100 µg. in the first week in the case of LA-2, 200 µl. or 200 µg. in the second week in the case of LA-2 and 300 µl. or 300 µg. in the third week in the case of LA-2.

The following Table 2 shows that scid mice, untreated or treated with NMS, develop clinical and histopathological indications of arthritis or carditis and hepatitis after 12 days. On the other hand, the administration of the monoclonal antibody LA-2 brings about a distinct reduction of the symptoms in the case of scid mice. Clinically, there were only ascertained slight reddenings of the joints and histopathologically only marginal changes. Mice treated with IMS showed no clinical findings of arthritis.

A detection of Borrelia burgdorferi organisms by in vitro culturing only succeeded in the case of mice which were either untreated or treated with NMS. In the case of mice treated with LA-2 or IMS, Borrelia burgdorferi organisms could not be detected (Table 2).

TABLE 2

| mouse strain C.B-17 scid | treatment with anti-serum | arthritis (after 12 days) | | carditis/hepatitis | B. burgdorferi detection (culture) |
|---|---|---|---|---|---|
| | | clinical | histopathological | histopathological | |
| n = 3 | — | + | + | + | + |
| n = 3 | NMS | + | + | + | + |
| n = 2 | IMS | − | − | − | − |
| n = 3 | LA-2 | −° | −°° | − | − |

° = slight reddening of the joint
°° = only marginal change

EXAMPLE 3.

Expression Cloning of the 3 lkD Antigen (OspA) of Borrelia burgdorferi ZS7.

High molecular weight DNA from the Borrelia burgdorferi strain ZS7 was purified after culturing in modified Kelly's medium. The spirochetes were pelleted by centrifuging at 10.000 g and washed three times with PBS buffer. The dry pellet was resuspended in 10 ml. TE (10 mmole/liter Tris, 1 mmole/liter EDTA, pH 7.4), treated with lysozyme (5 mg./ml.) for 15 minutes at 30° C. and the DNA released by the addition of 1 ml. 20% SDS. After the addition of 1.5 ml. sodium chloride solution (5 mole/liter), the solution was extracted with an equal volume of phenol, followed by an extraction with chloroform. The DNA was then precipitated by the addition of 2 volumes of absolute ethanol and incubation at −20° C. overnight. After centrifugation,the pellet was dissolved in 0.5 ml. TE and incubated with DNAse-free RNAse A (20 k g./ml.) for 45 minutes at 55° C., followed by treatment for 1 hour with proteinase K (0.1 µg./ml.) at 37° C. The solution was adjusted to 0.3 mole/liter sodium acetate and extracted with phenol-chloroform as described above. After precipitation with ethanol, the DNA was dissolved in TE.

Preparation of the Gene Bank.

High molecular weight DNA was randomlly sheared by sonication for 3 seconds. T4-DNA polymerase (30 minutes at 37° C.) and Klenow enzyme (5 minutes at 20° C.) were used in order to/fill in the single stranded ends of the generated DNA fragments. Blunt ended DMA was ligated into the BamHI site of an expression vector pUELXl by usin q an adaptor cloning strategy (see Bresan and Stanley, Nucl, Acid Res., 1987, p. 1056). After size selection by molecular sieve chromatography over Sephacryl S-1000 and transformation of competent host cells Escherichia coli (MC 1061), the percentage of recombinant clones was determined as follows: randomly selected colonies were picked and cultured to saturation in 2 ml. of selection medium (LB with 25 µg./ml. of ampicillin). The plasmid DNA was isolated according to the usual alkaline lysis method and subsequently cleaved with BamHI. More than 50% of the analysed plasmids contained, were found to count DNA-inserts with an average size of>1.5 kb.

Plating and Expression Screerina of the Borrelia burgdorferi ZS7 gene bank.

The cells were plated on 24×24 cm. plates at a density of 7000 colonies per plate and incubated overnight at 300°C. After transfer of thelcolonies to nitrocellulose filters(NC), the expression of μ-galactosidase fusion proteins was induced by incubation for 2 hours at 42° C. The filters were transferred to a Whatman 3MM paper which had been treated with 5% SDS and incubated for about 25 minutes at 95° C. The proteins were then electro-blotted with the use of a conventional Western blotting apparatus. After DNAse treatment of the NC filters, immune-reactive clones were identified by an expression screening with the use of monoclonal antibodies. Non-specific binding sites on the NC filters were blocked by incubation for 4 hours with PBS containing 0.2% w/v of gelatine and 3 mmole/liter sodium azide at room temperature. Subsequently, the filters were incubated for 18 hours with continuous shaking with culture supernatants of the anti-31 kD monoclonal antibody LA-2. After extensive washing (PBS+1% v/v Triton X-100; PBS+ 0.5 mole/liter sodium chloride; PBS+1 mole/liter sodium chloride; each step 10 minutes), the filters were incubated with a 1:10000 dilution of a peroxidase-labelled F(ab)$_2$ preparation of rabbit-anti-mouse-IgG antibodies for 1.5 hours at room temperature with permanent shaking. The filters were again washed as described above and then incubated with diaminobenzidine as peroxidase substrate. Of $10^4$ recombinant clones, 20 clones reacted with the monocloanl antibody LA-2.

Secuence Analysis of the 31 kD Antigen (OspA).

The insert DNA of a recombinant *Escherichia coli* clone with positive antibody reaction with IA-2 was analysed and sequenced according to standard protocols (Maniatis et al., (1982) Molecular Cloning; A Laboratory Manual, Cold Spring Harbor Laboratory, Cold Spring Harbor). The DNA insert of this clone contained the OspA gene coding for the *Borrelia burgdorferi* 31 kD antigen in full length. The plasmid which contains the OspA gene was designated pZS-7/31-2 and was deposited according to the Budapest Convention at the DSM under the number DS5528.

The recombinant protein produced by this immune-positive clone was designated as rZS7/31-2. The DNA sequence of the OspA gene was determined. It is shown in FIG. 1 of the accompanying drawings, together with the amino acid sequence of the OspA protein deduced from the DNA sequence.

From FIG. 1, it can also be seen that the 31 kD antigen from *Borrelia burgdorferi* corresponds to a protein of 1273 amino acids.

Preparation of Non-Fusion Proteins.

a) The clone which expresses the immune-reactive protein rZS7/31-2 was cultured overnight at 300° C. in 10 ml. LB with ampicillin. 1 ml. of the culture was introduced into the selection medium and cultured at 30° C. with good aeration up to saturation.

After cooling and centrifugation,the cells were washed in STE buffer (10 mmole/liter Tris, 100 mmole/liter sodium chloride, 1 mmole/liter EDTA, pH 8.0) and the pellet resuspended in 0.6 ml. of lysis buffer (25% sucrose,. 50 mmole/liter Tris, pH 8.0). After the addition of 150 μl. of lysozyme (10 mg./ml.), the mixture was incubated for 15 minutes on ice, followed by a further incubation (15 minutes on ice) with 18 μl. DNAse 1 (10 mg./ml.) in the presence af 5 μl. of 1 mole/liter magnesium chloride. Finally, 250 μl. 4× detergent mixture (1% Triton X100, 0.5% deoxycholate, 0.1 mole/liter sodium chloride, 10 mmole/liter Tris, pH 7.4) were added, followed by an incubation on ice for 5 minutes. After centrifugation,the pellet was washed twice with buffer A (50 mmole/liter Tris, 50 mmole/liter sodium chloride, 1 mmole/liter EDTA, pH 8.0) and resuspended in 9 volumes of buffer A contained 8M urea and incubated for 1 hour at room temperature. The sample was diluted with 9 parts of buffer B (50 mmole/liter monopotassium dihydrogen phosphate/dipotassium monohydrogen phosphate, 50 mole/liter sodium chloride, 1 mmole/liter EDTA, pH 10.7) and stirred for 30 minutes at room temperature, the pH being maintained at 10.7 by the addition of potassium hydroxide solution. After adjustment of the pH of the solution to 7.0 by the addition of hydrochloric acid, the sample was dialysed overnight against buffer A at 4° C. and centrifuged for 10 minutes at 4°C. and 10,000 r.p.m. in an SS34 rotor. The supernatant, which contains the recombinant protein, was stored at −20° C.

b) Since the clone also secretes the immune-reactive protein rZS7/31-2 into the culture medium, a purification (affinity chromatography) directly from the culture supernatant was performed.

Preparation of Recombinant OspA (non-fusion) Protein and Purification by Affinity Chromatography.

The recombinant proteins were subsequently purified by affinity chromatography. For this purpose, purified monodonal antibodies LA-2 were covalently bound to activated Sepharose CL 4B. The dialysed urea extract or the culture supernatant with the recombinant protein was adsorbed on mouse IgG-Sepharose CL 4B and subsequently passed over the LA-2-Sepharose CL 4B column. After intensive washing, the bound recombinant protein was eluted with 0.1 mole/ liter glycine/hydrochloric acid - 0.1 mole/liter sodium chloride, pH 2.5. The pH value of the collected fractions was immediately adjusted to neutral by the addition of 1/1o volume of 0.5 mole/liter dipotessium monohydrogen phosphate. The protein-containing fractions were concentrated and dialysed. The degree of purification was determined by SDS-polyacrylamide gel electrophoresis.

Immunological Characterisation of the Recombinant Protein rZS7/31-2.

The recombinant protein rZS?/31-2 was investigated immunologically . For comparison, recombinant protein rB31/41-9 (*Borrelia burgdorferi* 41 kD surface antigen) was used.

Flat-bottomed microtitre plates were coated with urea extracts of the recombinant proteins rZS7/31-2 and rB31/41-9 or with a urea extract of the *Escherichia coli* strain MC 1061 used for the gene expression. Non-specific binding sites were blocked by incubation with 0.2% gelatine in phosphate-buffered sodium chloride solution.

Microtitre plates were incubated with the given monoclonal antibodies LA-2 (anti-31 kD, OspA), LA-1 (anti-41 kD, flagellin) or ACET_2 (anti-$\alpha_1$-antichymotrypsin).

Bound monoclonal antibodies were detected via peroxidase-labelled, species-specific anti-mouse immuno globulins. Bound peroxidase-labelled antibodies were quantified by using the peroxidase substrate o-phenylenediamine. The adsorption at 492 nm ($A_{492}$) was determined directly in the microitire plates with the help of an automated plate photometer. The adsorption is proportional to the amount of bound monoclonal antibodies.

The monoclonal antibody LA-2 reacts in a specific manner with rZS7/31-2 but not with MC 1061 or rB31/41-9. For control reaction the monoclonal antibody.LA-1which is specific for rB31/41-9 is used. The monoclonal antibody ACHT_2 (negative control) does not show a significant reaction on any of the proteins.

FIG. 2 of the accompanying drawings shows that the antigenic epitope recognized in a specific manner by the monoclonal antibody LA-2 is expressed on the recombinant protein rZS7/31-2 which was cloned from the genome of *Borrelia burgdorferi* ZS7.

EXAMPLE 4.

Comparison of Antibodies Specific for the 31 kD (Ospa) or the 34 kD Antigen (OspB) and Antibodies which are Specific for the 41 kD Antigen (Flagellin).

The monoclonal antibodies LA-2 and LA-26.1 recognize the 31 kD antigen OspA and are of the isotype IgG2b and IgG1, respectively. The monoclonal antibodies LA-25.1 and LA-27.1 recognize the 34 kD antigen OspB and are of the isotype IgG2B and IgG1, respectively . The monoclonal antibodies LA-10 and LA-21 are specific for the flagella-associated 41 kD periplasmatic protein (flagellin) of *Borrelia burgdorferi* and are of the isotype IgG2a and IgG1, respectively. All the above-mentioned antibodies were obtained according to the process described in Example 2. In this experiment, it is to be ascertained whether monoclonal antibodies against another *Borrelia burgdorferi* antigen in scid mice also confer protection against the clinical symptoms of lyme borreliosis.

(LA-10 or LA-21) showed clinical signs of arthritis, the pathological changes typical for untreated scid mice (see the following Table 3). The severity of the symptoms in the last-mentioned animals increased with increasing period of time after the inoculation and did not weaken during the period of observations No spirochetes could be isolated from scid mice which had previously been treated either with anti-ZS7IMS or with the antibody LA-2. In contrast the detection of Spirochaetes by immunofluorescence and by culturing of blood from scid mouse was possible in those mice which had been treated with PBS buffer, NMS or the monoclonal antibodies LA-25.1, LA-26.1, LA-27.1, LA-10 or LA-21.

TABLE 3

| mouse strain C.B-17 scid (number of mice) | treatment with | IgG subtype | clinical arthritis | histopath- ology peri- arthritis/ arthritis | carditis | detection of B. burgdorferi (culturing and immunofluorsecence) |
|---|---|---|---|---|---|---|
| n = 8 | PBS (negative control) | | + | + | + | + |
| n = 3 | NMS (negative control) | | + | + | + | + |
| n = 3 | anti-B31 IMS | | − | − | −⁺ | +° |
| n = 2 | anti-ZS7 IMS | | − | − | −⁺ | − |
| n = 6 | LA-2 (OspA) | 2b | − | −⁺ | −⁺ | − |
| n = 3 | LA-10 (flagellin) | 2a | + | + | + | +° |
| n = 3 | LA-21 (flagellin) | 1 | + | + | +/− | + |
| n = 3 | LA-26.1 (OspA) | 1 | ± | ± | ± | +° |
| n = 3 | LA-25.1 (OspB) | 2b | ± | ± | ± | + |
| n = 3 | LA-27.1 (OspB) | 1 | ± | ± | ± | +° |

The degree of the histopathological change is indicated as follows: − none; −⁺ subclinical; +/− moderate; + severe.
o A detection of *Borrelia burgdorferi* by immunofluorescence was not possible in all investigated individuals.

The polyclonal anti-B31 immune serum (IMS) was taken from C57BL/6 mice 91 days after a subcutaneous inoculation with 1×10⁸ *Borrelia burgdorferi* B31 organisms. The polyclonal anti-ZS7 IMS was taken from C57BL/6 mice 68 days after a subcutaneous inoculation with 1×10⁸ *Borrelia burgdorferi* ZS7. Both sera contained 60 μg./ml. of specific antibodies, as was determined in an ELISA system (see Schaible et al., J. Exp. Med., 170, 1427-1432/1989). The normal mouse serum (NMS) was taken from non-infected C57BL/6 mice.

At the point of time of the inoculation and there after in 4 day intervals, the given antibodies, the IMS, the NMS or PBS buffer were passively transferred intra-peritoneally into scid mice according to the following protocol:

day 0 and day 3: 100 μl.
day 7 and day 10: 200 μl.
day 13 and day 17: 300 μl

Scid mice which had been treated either with anti-ZS7IMS, anti-B31IMS or with the the monoclonal antibody LA-2 showed no visible clinical symptoms of arthritis, i.e. no reddening and swelling of tibiotarsal joints occurred during the 21 days of observation. Also, no symptoms of carditis and hepatitis were ascertained. Histopathological investigations showed no changes in the joints, the heart and the liver of scid mice which had been treated either with anti-ZS7-IMS, anti-B31 IMS or with the monoclonal antibody LA-2.

The other OspA-specific monoclonal antibodies LA-26.1 of the isotype IgG1, as well as the OspB-specific antibodies LA-25.1 and LA-27.1, were able to mitigate the clinical symptoms of arthritis, carditis and hepatitis. Slight pathological changes in the investigated organs were here shown.

In contrast, scid mice which had been treated either with PBS buffer, NMS or monoclonal antibodies against flagellin

EXAMPLE 5.

Action of Antiserum from Mice Immunised with OspA on the Course of Lyme Borreliosis in scid mice.

In this experiment, it could be shown that an administration of native OspA (isolated from *Borrelia burgdorferi* strain ZS7) or of recombinant OspA (isolated from

*Escherichia coli* bacteria which had been transformed with the recombinant plasmid pZS7/31-2 (DSM 5528)) into normal mice (mice strain C57BL/6) induced the formation of protective polyclonal antibodies. If these antibodies are administered to scid mice, there is brought about a protection against Lyme borreliosis. It is thereby ascertained that recombinant OspA induces a protective immune response comparable to that induced with native OsPA. The results and the details of carrying out of this experiment are given in the following Table 4.

The obtaining of recombinant OspA is described in Example 3.

The obtaining of native OspA, as well as the immunising of mice with OspA, took place as follows:

Enrichment of Native 31 kDa OspA.

3.2×10¹⁰ spirochetes are stirred with a magnetic stirrer for 2 hours at 4° C. in 5 ml. of PBS/7.5 ml. n-butanol in the presence of protease inhibitor (5 mmole/liter EDTA, 5 mmole/liter benzamidine and 0.5 mmole/liter PMSF). Thereafter, the mixture is centrifuged for 90 minutes at 10,000 r.p.m. in a Sorvall centrifuge (fixed-angle rotor). The aqueousphase which contains the surface proteins is removed and washed three times with chloroform. The protein content is determined via the extinction at 280 nm or with the BCA test.

In the silver gel or Western blot with anti-*Borrelia burgdorferi* rabbit serum, there was found for strain ZS7 a main band in the molecular weight range of 31 kDa, as well as weak bands at 20, 34, and 65–68 kDa. The butanol/water preparation of *Borellia burgdorferi* strain B31 gave a main band at 31 kDa, as well as weak bands at 20 and 34 kDa.

Immunisation of Mice with Native and Recombinant OsPA.

To C57BL/6 and C.B-17 mice were given three times subcutaneously into the root of the tail at an interval of 7 to 10 days 5 g. (native OspA of strain B31) or 10 µg. (native OspA of strain ZS7, recombinant OspA of ZS7) in 100 µl. of adjuvant (ABM3; firm Sebak, Aidenbach, Federal Republic of Germany). At the earliest 3 weeks after the last immunisation, serum could be taken for 3 to 4 months. The content of specific antibodies is determined in the ELISA system.

TABLE 4

Effect of *Borrelia burgdorferi*-specific monoclonal and polyclonal antibodies on spirochaetosis and development of arthritis in scid mice infected with *Borrelia burgdorferi*

| mouse strain C.B-17 scid (number of mice) | treatment with | development of arthritis after week(s) | | | detection of *B. burgdorferi* |
|---|---|---|---|---|---|
| | | 1 | 2 | 3 | |
| n = 6 | PBS (negative control) | ± | + | + | 6/6 |
| n = 6 | LA-2 | – | – | – | 0/3 |
| n = 2 | anti-OspA (native) IMS | – | – | – | 0/2 |
| n = 3 | anti-OspA (recomb,) IMS | – | – | – | 0/3 |

First antibody transfer i.p. (100 µl) day 0 (day of the inoculation with *B. burgdorferi* strain ZS7, $1.10^8$ organisms, s.c. into the root of the tail). Further antibody transfers day 4 (100 µl.), day 7 (200 µl.), day 11 (200 µl.), day 14 (300 µl.), day 18 (300 µl.),(i.p.).

We claim:

1. A vaccine against Lyme disease comprising a monoclonal antibody selected from the group consisting of LA-2 secretrd hybridoma cell line ECACC 89091302, LA-25.1 secreted by hybridoma cell line ECACC 90050405, LA-26.1 secreted by hybridoma cell line ECACC 90050406, and LA-27.1 secreted by hybridoma cell line ECACC 90050407 which binds to at least one antigen selected from the group consisting of OspA and OspB of *Borrelia burgdorferi*, strain ZS7, wherein said antibody is characterized by conferring passive immunity against Lyme disease in a subject to which it is administered.

2. The vaccine of claim 1, wherein said antibody is of the IgG isotype.

3. The vaccine of claim 1, further comprising a carrier or an adjuvant.

4. A method for the treatment of Lyme disease comprising administering to a mammal in need thereof an amount of the vaccine of claim 1, sufficient to confer passive immunity against Lyme disease in a subject to which it is administered.

5. A method of treating Lyme disease associated arthritis, carditis, or hepatitis comprising administering the vaccine of claim 1.

6. The vaccine of claim 1, wherein said monoclonal antibody is LA-2, which is secreted by hybridoma cell line ECACC 89091302.

* * * * *

UNITED STATES PATENT AND TRADEMARK OFFICE
CERTIFICATE OF CORRECTION

Page 1 of 2

PATENT NO. : 5,780,030
DATED : July 14, 1998
INVENTOR(S) : Markus M. Simon, et al.

It is certified that error appears in the above-identified patent and that said Letters Patent is hereby corrected as shown below:

In column 1, line 15, change "Borrelis" to -- Borrelia --.

In column 1, line 51, change "Licrobial" to -- Microbial --.

In column 2, line 27, change "hybridoms" to --hybrodomal--.

In column 3, line 13, change "invention--,and add-- . -- after invention.

In column 6, line 11, change "chances" to -- changes --.

In column 7, line 19, change "myeloms" to -- myeloma --.

In column 7, line 24, change "A pter" to -- After --.

In column 7, line 54, change "Borrelis" to -- Borrilia --.

UNITED STATES PATENT AND TRADEMARK OFFICE
CERTIFICATE OF CORRECTION

PATENT NO. : 5,780,030
DATED : July 14, 1998
INVENTOR(S) : Markus M. Simon, et al.

It is certified that error appears in the above-identified patent and that said Letters Patent is hereby corrected as shown below:

In column 8, line 49, change "DMA" to -- DNA --.

In column 8, line 50, change "usin" to -- using --.

In column 8, line 51, delete "q".

In column 8, line 67, change "the1colonies" to -- the colonies --.

In column 9, line 43, change "1273" to -- 273 --.

In column 9, line 47, change "300°C" to -- 30° --.

In column 10, line 18 and line 19, change "mon-odonal" to -- mom-oclonal --.

In column 10, line 45, change "ACET_2" to -- ACHT_2 --.

In column 12, line 7, change "observations" to -- observation --.

Signed and Sealed this

Thirteenth Day of June, 2000

Attest:

Q. TODD DICKINSON

*Attesting Officer*  *Director of Patents and Trademarks*